(12) United States Patent
Taylor et al.

(10) Patent No.: US 9,606,087 B1
(45) Date of Patent: Mar. 28, 2017

(54) ULTRASONIC NEAR-SURFACE INUNDATION TESTING DEVICE

(71) Applicant: The United States of America as Represented by The Secretary of the Army, Washington, DC (US)

(72) Inventors: Oliver-Denzil S. Taylor, Vicksburg, MS (US); Katie E. Martin, Vicksburg, MS (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 14/920,385

(22) Filed: Oct. 22, 2015

(51) Int. Cl.
*G01N 33/24* (2006.01)
*G01N 29/04* (2006.01)

(52) U.S. Cl.
CPC ............ *G01N 29/04* (2013.01); *G01N 33/24* (2013.01); *G01N 2291/023* (2013.01)

(58) Field of Classification Search
CPC ... A01B 12/06; G01N 29/04; G01N 2291/023
USPC .......................................................... 73/594
See application file for complete search history.

(56) References Cited

U.S. PATENT DOCUMENTS

| | | | | |
|---|---|---|---|---|
| 3,457,777 A * | 7/1969 | Nielsen | ................... | G01N 3/08 73/84 |
| 5,265,461 A * | 11/1993 | Steiger | ................... | G01N 29/07 73/38 |
| 5,275,063 A * | 1/1994 | Steiger | ................. | G01N 33/241 73/865.6 |
| 6,834,554 B2 * | 12/2004 | Shen | ........................ | G01N 3/24 73/821 |
| 7,216,555 B2 * | 5/2007 | Drummond | .......... | A01B 79/005 73/864.45 |

\* cited by examiner

Primary Examiner — J M Saint Surin
(74) Attorney, Agent, or Firm — Brian C. Jones

(57) ABSTRACT

An ultrasonic near-surface inundation testing (UNIT) device includes a soil cell device, a head tank feeding fluid into the soil cell and a reservoir tank feeding fluid into the head tank. The soil cell device includes a substantially planar base, at least one removable top plate with at least one pressure equalization port, at least one bottom plate, at least one sample chamber holding a soil sample, bender ports and a bender sensor pair. The base connects to chamber posts. The top plate connects to the chamber posts and has a cell inlet receiving fluid from the head tank. The bottom plate connects to the chamber posts and has a cell outlet passing fluid to the reservoir tank. The sample chamber, including at least one removable chamber plate, is located between the top and bottom plates. The bender sensor pair extend into the sample chamber through the bender ports.

20 Claims, 12 Drawing Sheets

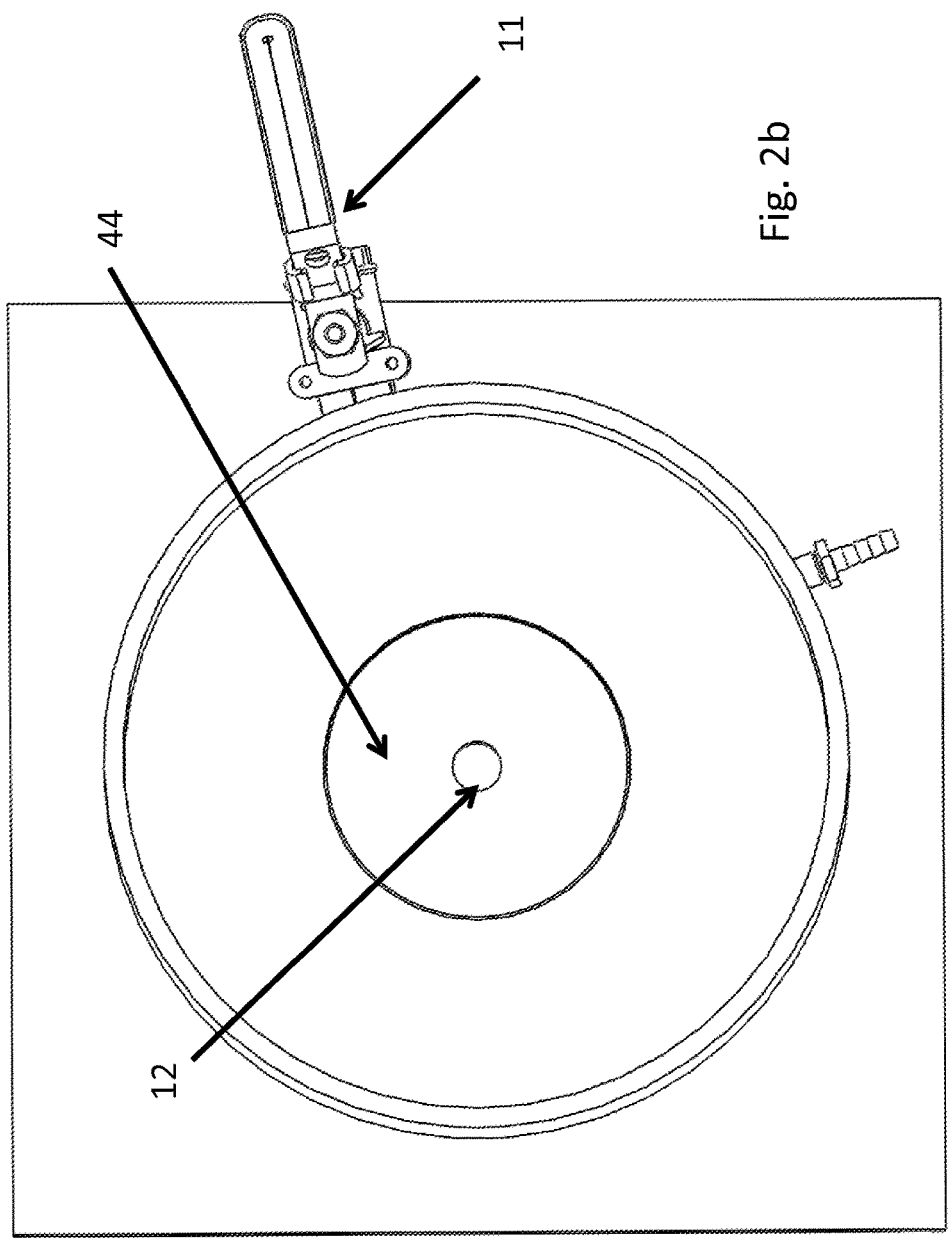

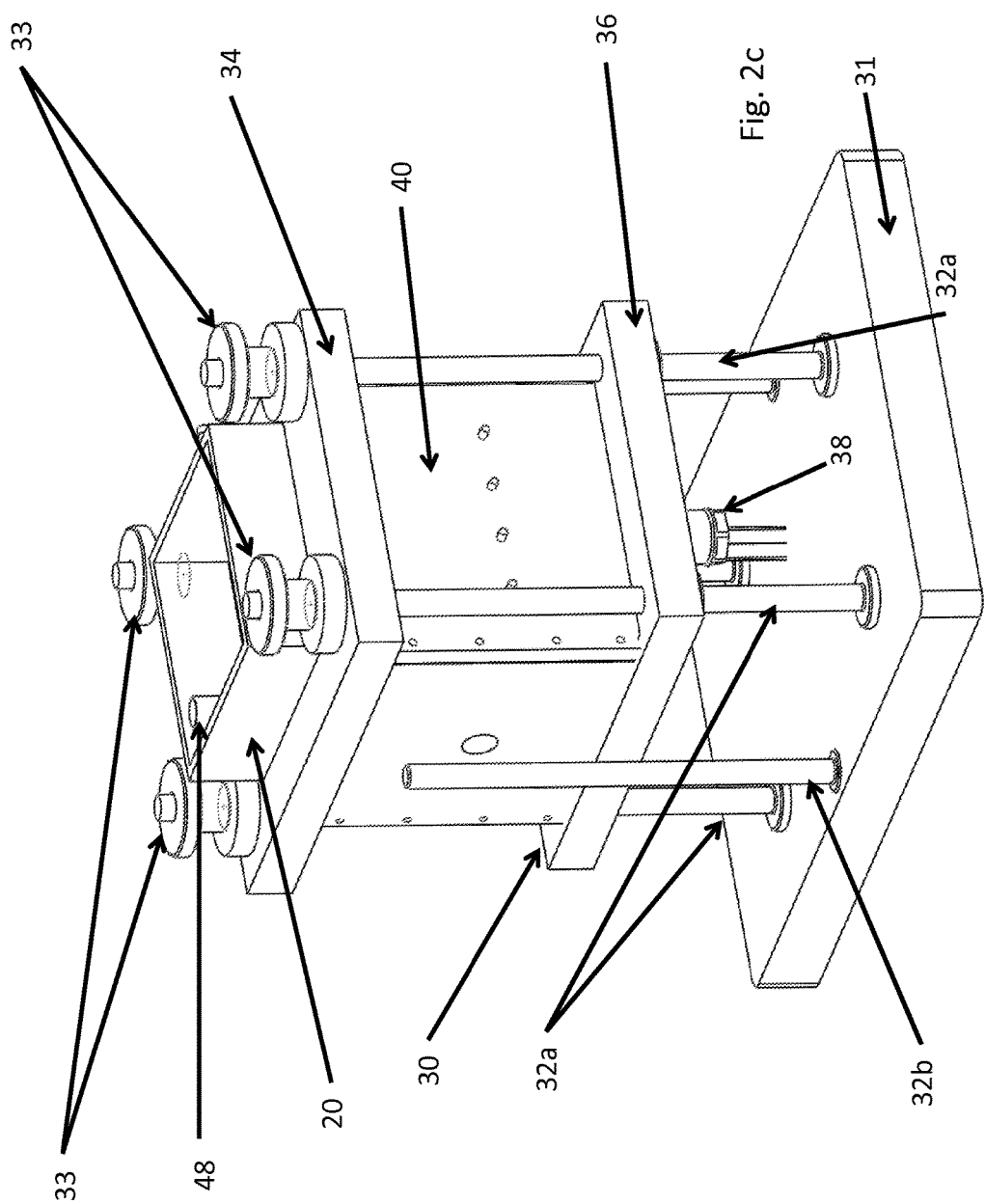

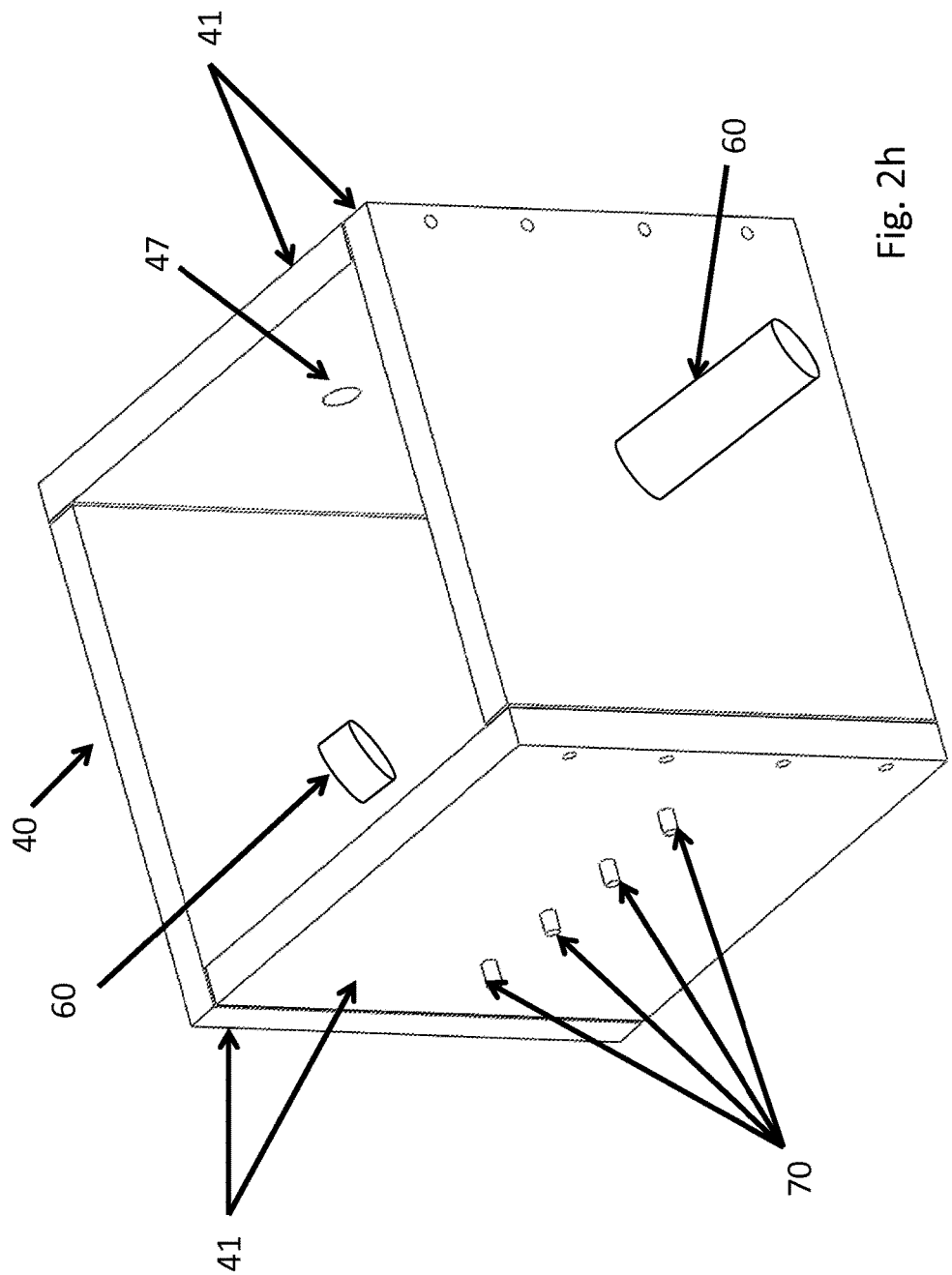

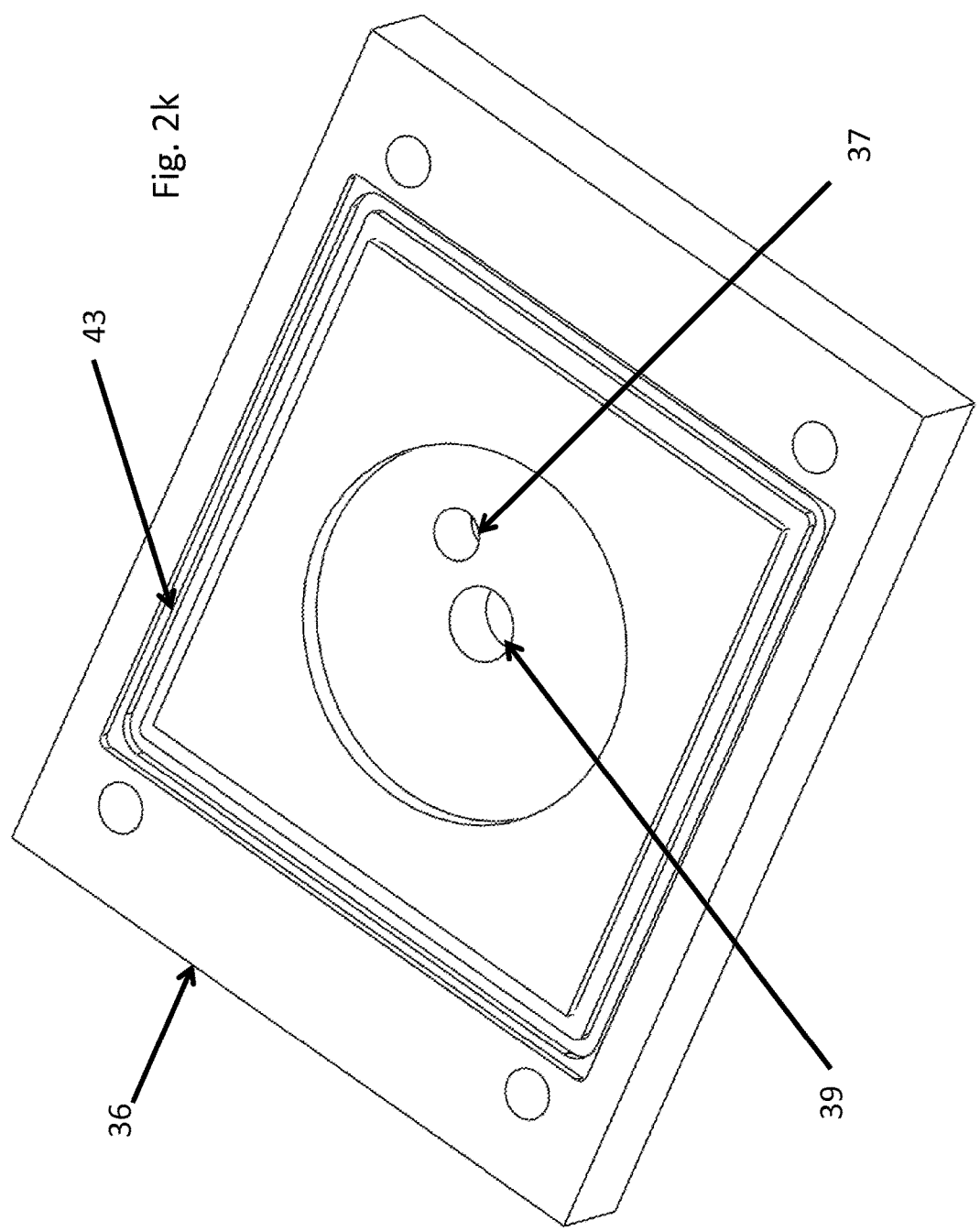

ULTRASONIC NEAR-SURFACE INUNDATION TESTING DEVICE

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

BACKGROUND OF THE INVENTION

1. Field of Invention

This invention relates to the field of soil testing and more specifically to a device for testing soil samples in a simulated environment.

2. Description of Related Art

Seismic sensor systems process surface and subsurface waves for source classification, location, and identification of specific targets of interest. Federal agencies such as the US Army Corps of Engineers, the US Geological Survey and the Department of Homeland Security use shallowly buried seismic monitoring technologies to monitor and evaluate localized security and infrastructure hazards across a wide range of environments. Military sensor systems and technologies must be self-adapting for new environments and soil profiles.

The widespread use of shallow seismic sensor systems has increased the importance of understanding seismic response variability for different soil profiles, geological conditions, environments and climates. Researchers develop seismic characteristics for seismic sensor systems in specific soils under ideal field conditions. However, real-world conditions present more complex problems, introducing variables such as different soil types, fluid flow, drainage and varying soil moisture levels that cause changes in seismic wave propagation. Furthermore, these tests occur when the soil is under compression or "confinement", preventing the tests from modeling the low-to zero-confinement conditions of near-surface environments. Seismic sensor systems may perform inaccurately during rainfall and in environments with higher soil moisture levels due to the inability of idealized characteristics to accommodate these changes.

There is an unmet need in the art for equipment to test the effects of both static and dynamic fluid on seismic wave propagation under near-surface conditions.

BRIEF SUMMARY OF THE INVENTION

A soil cell device includes a substantially planar base, at least one top plate, at least one bottom plate, at least one sample chamber, a plurality of bender ports and a bender sensor pair. The substantially planar base connects to a plurality of chamber posts. The top plate connects to the chamber posts and has a cell inlet. The bottom plate connects to the chamber posts and has a cell outlet. The sample chamber is located between and in contact with the top plate and the bottom plate. The sample chamber includes at least one chamber plate. The bender ports extend into the sample chamber. The bender sensor pair extend into the sample chamber through the bender ports. The top plate and the chamber plate are removable from the soil cell device.

An ultrasonic near-surface inundation testing (UNIT) device includes a soil cell device, as above, at least one head tank, at least one reservoir tank and at least one recirculating pump. The head tank includes a head inlet, a head outlet and an overflow outlet. The overflow outlet is located at a first height above a bottom of the head tank. The reservoir tank includes a reservoir inlet and a reservoir outlet. The reservoir tank has a greater fluid capacity than the head tank. The reservoir outlet is connected to the head inlet. The overflow outlet is connected to the reservoir inlet. The head outlet is connected to the cell inlet. The cell outlet is connected to the recirculating pump. The recirculating pump is connected to the reservoir inlet

BRIEF DESCRIPTION OF SEVERAL VIEWS OF THE DRAWING(S)

FIGS. 2a-2k illustrate multiple partial views of an exemplary embodiment of the UNIT device.

TERMS OF ART

As used herein, the term "bender sensor pair" means a piezoelectric transmitter capable of transmitting a wave signal and a piezoelectric sensor capable of receiving the transmitted wave signal.

As used herein, the term "resistivity sensor" means a sensor capable of measuring a resistivity value of a material.

As used herein, the term "piezometric sensor pair" means a pair of piezoelectric sensors capable of measuring a pressure differential.

DETAILED DESCRIPTION OF THE INVENTION

Figure 1:
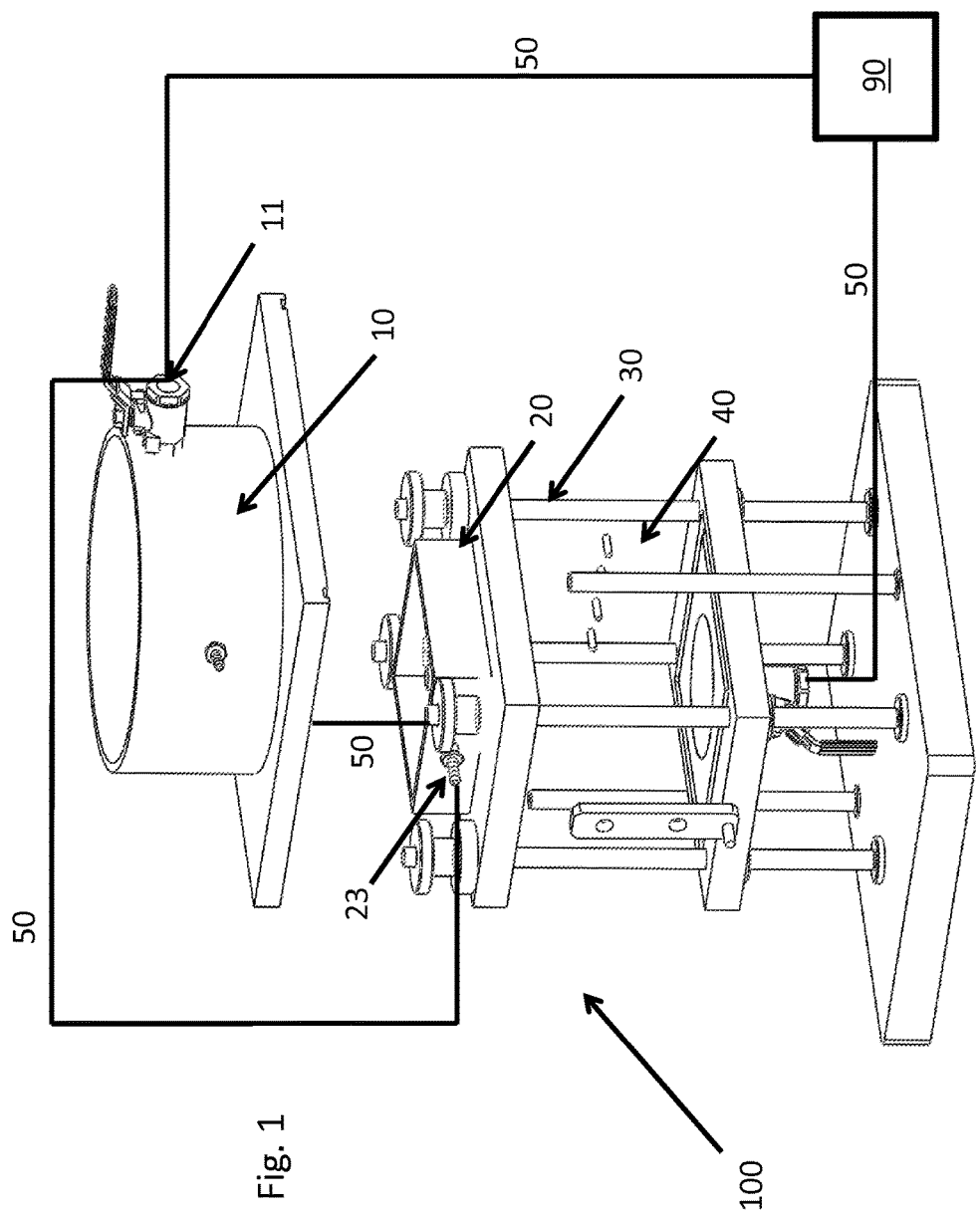
FIG. 1 illustrates an exemplary embodiment of an ultrasonic near-surface inundation testing (UNIT) device.

FIG. 1 illustrates an exemplary embodiment of UNIT device 100. UNIT device 100 includes at least one reservoir tank 10, at least one head tank 20, at least one soil cell 30 having at least one sample chamber 40 and at least one recirculating pump 90. Fluid conduits 50 interconnect reservoir tank 10, soil cell 30 and recirculating pump 90, allowing recirculating pump 90 to transfer fluid exiting soil cell 30 into reservoir tank 10. UNIT device 100 also includes at least one bender sensor pair 60, resistivity sensor 70 and/or piezometric sensor pair 80.

Reservoir tank 10 contains a volume of fluid used in soil tests. Fluid from various sources enters reservoir 10 through reservoir inlet 11 and exits to head tank 20. Fluid from reservoir tank 10 enters head tank 20 and exits to soil cell 30. Head tank 20 contains a smaller volume of fluid than reservoir tank 10 to ensure that fluid entering soil cell 30 simulates meteorological conditions and does not exert a force on the soil sample.

An overflow outlet 23 in head tank 20 ensures that fluid in excess of the desired volume returns to reservoir tank 10. In the exemplary embodiment, overflow outlet 23 is located at a height approximately 13.9 mm from the bottom of head tank 20, thus ensuring an approximately 13.9 mm head to simulate meteorological field conditions. Other head tanks 20 may vary the height of overflow outlet 23 to simulate different field conditions, resulting in a quasi-unique height for each overflow outlet 23.

Figure 2A:
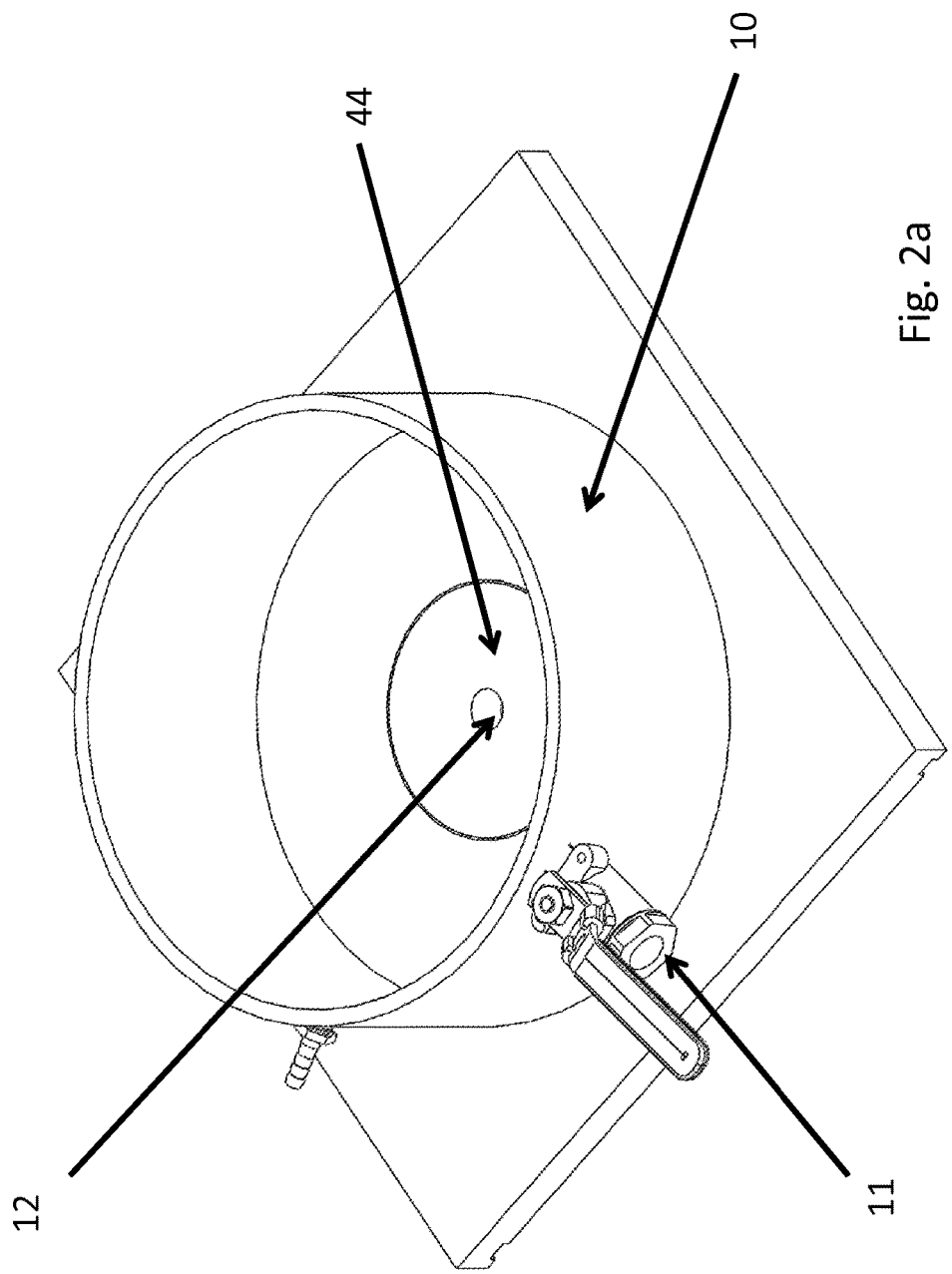
Figure 2D:
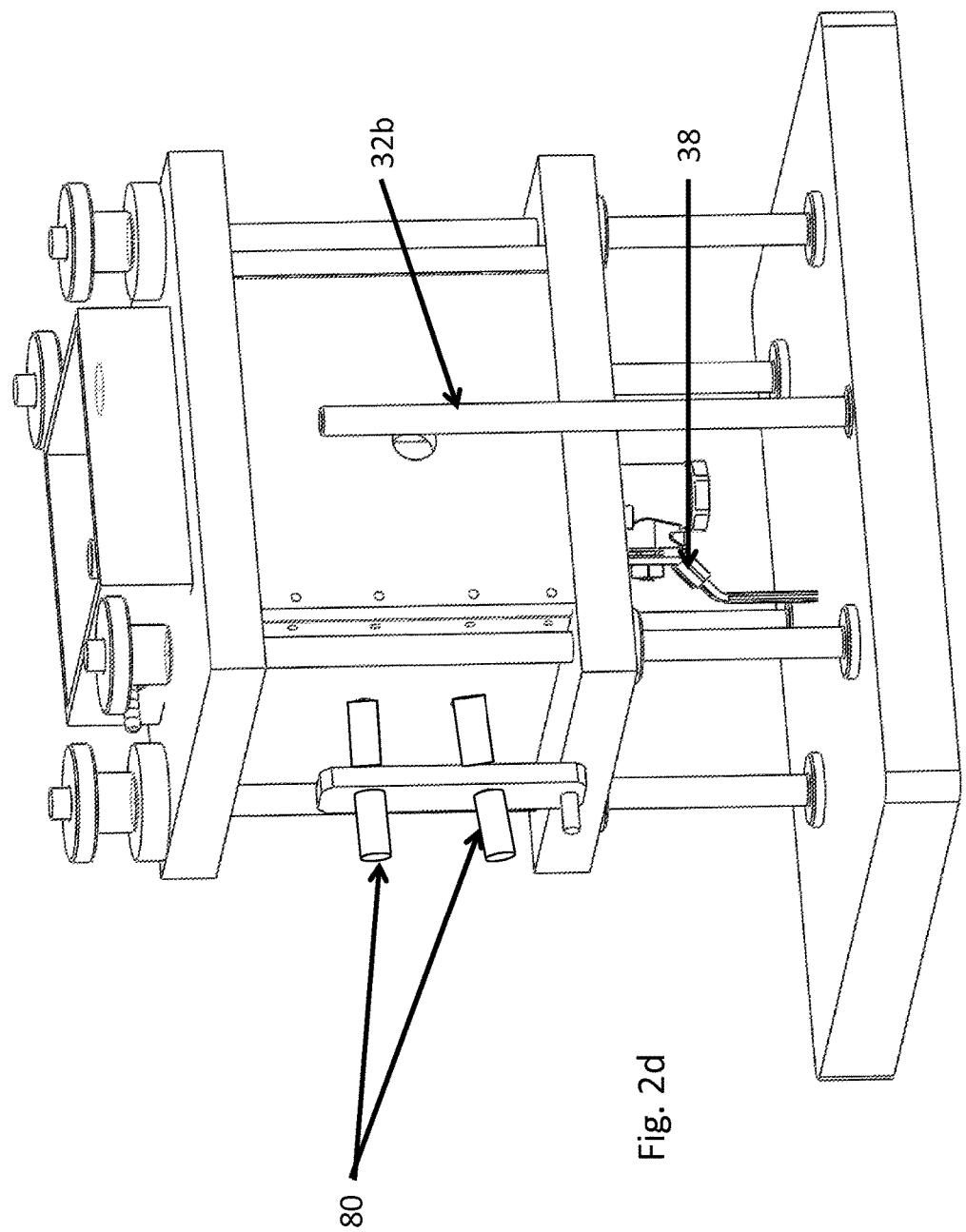
Figure 2E:
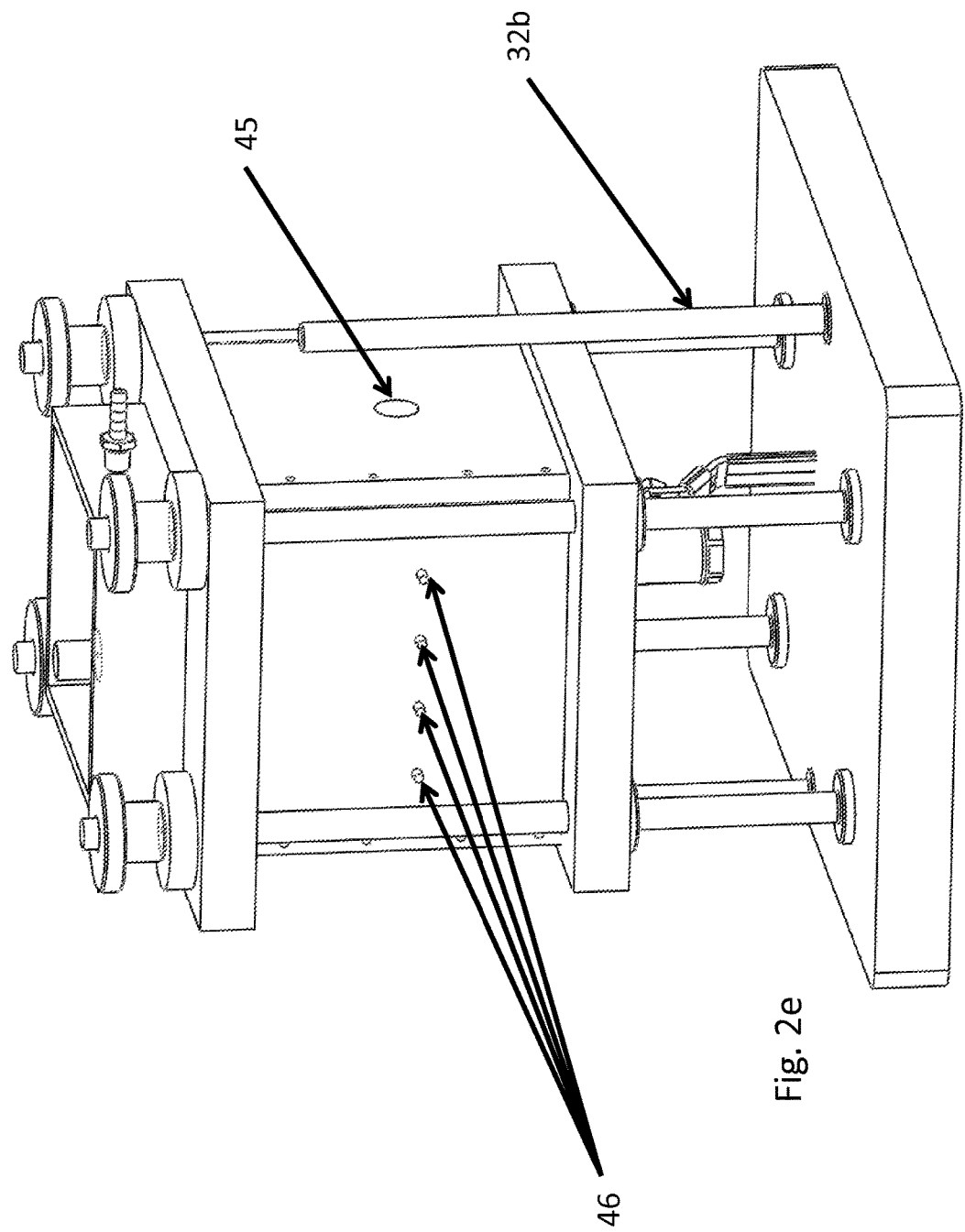
Figure 2F:
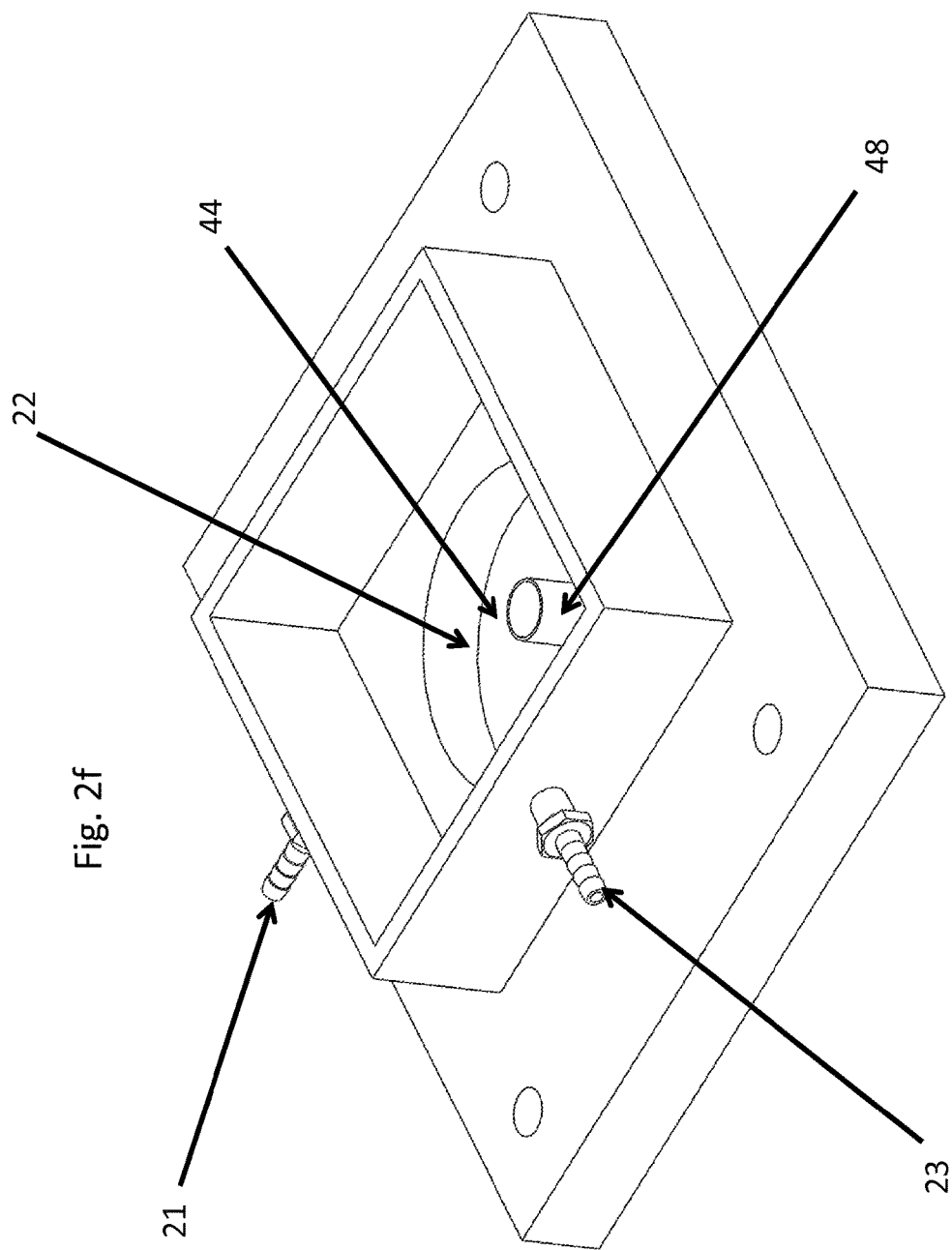
Figure 2G:
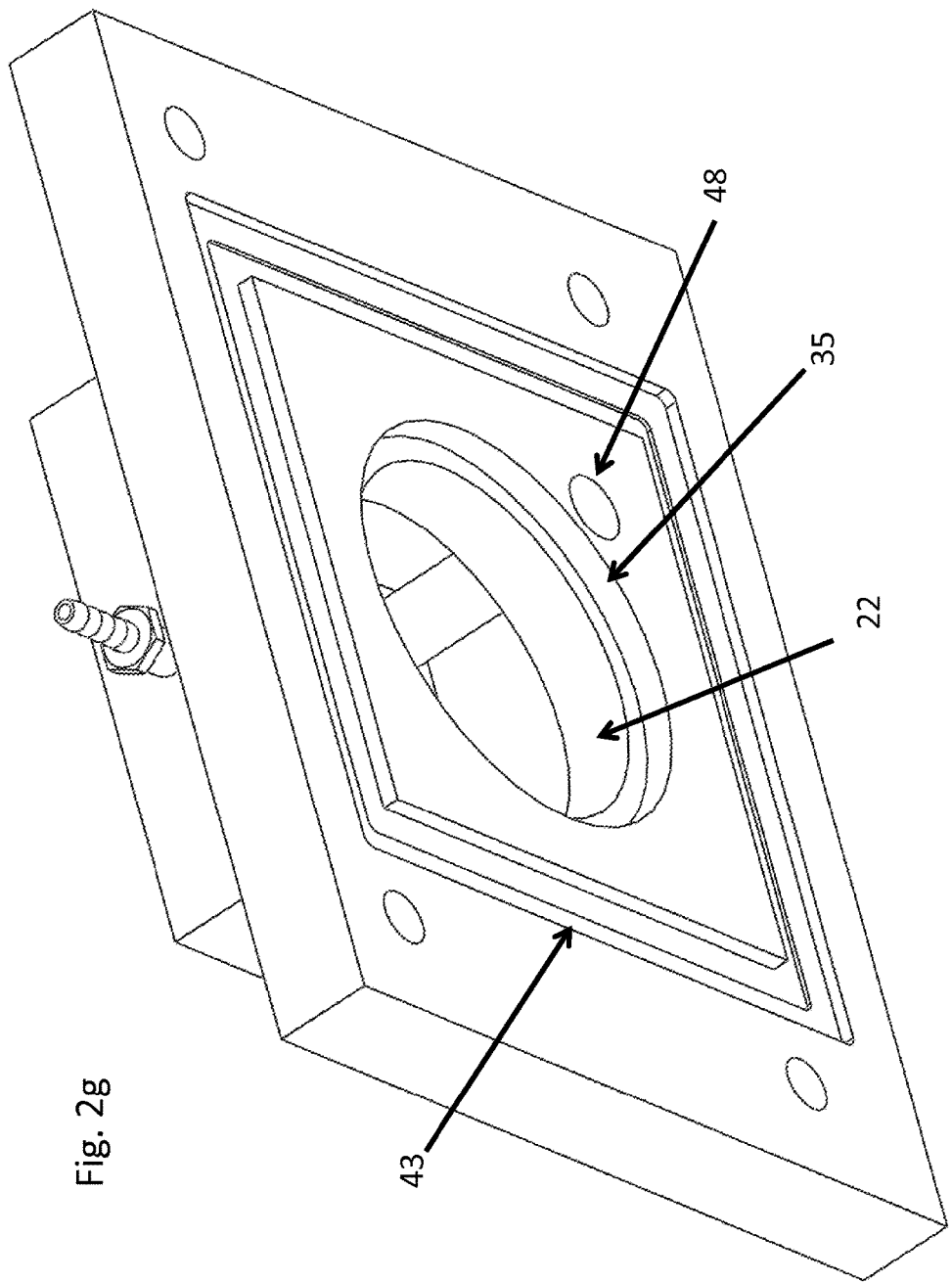
Figure 2I:
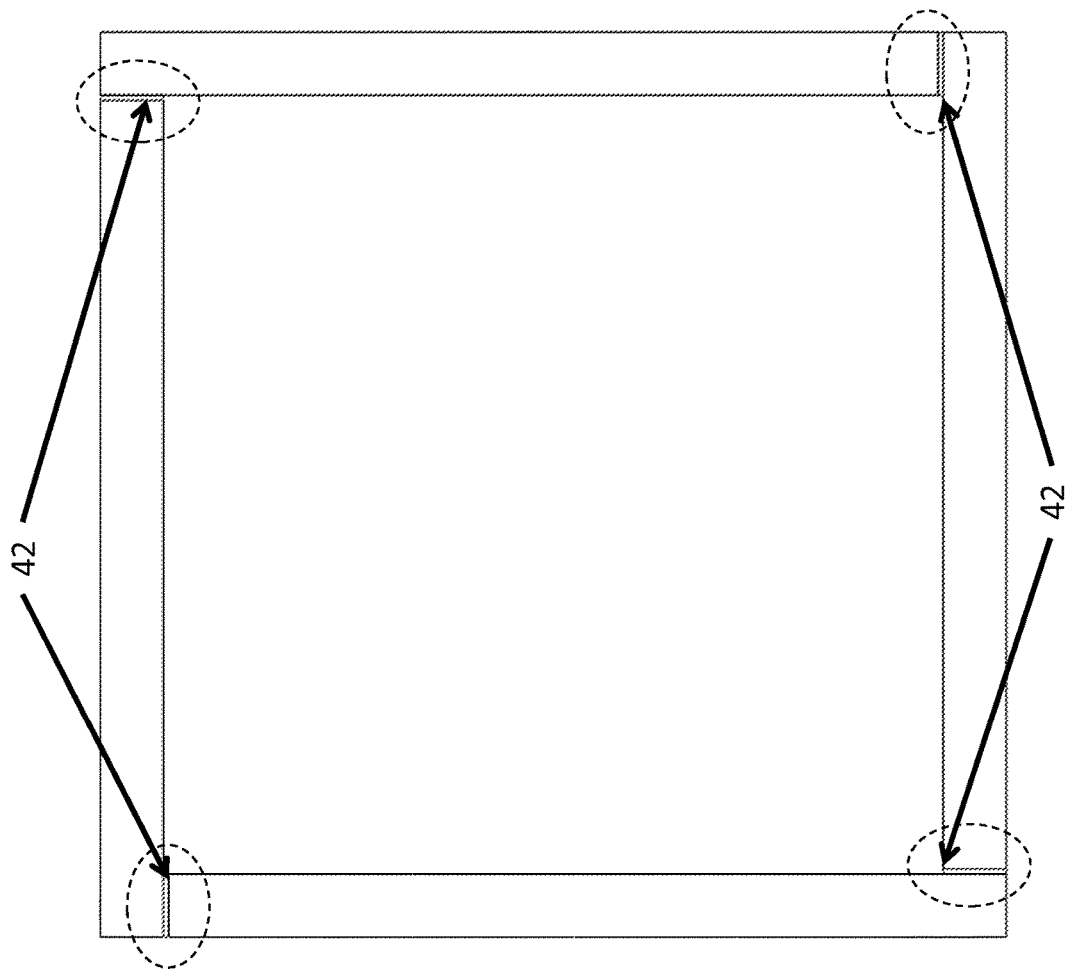
Figure 2J:
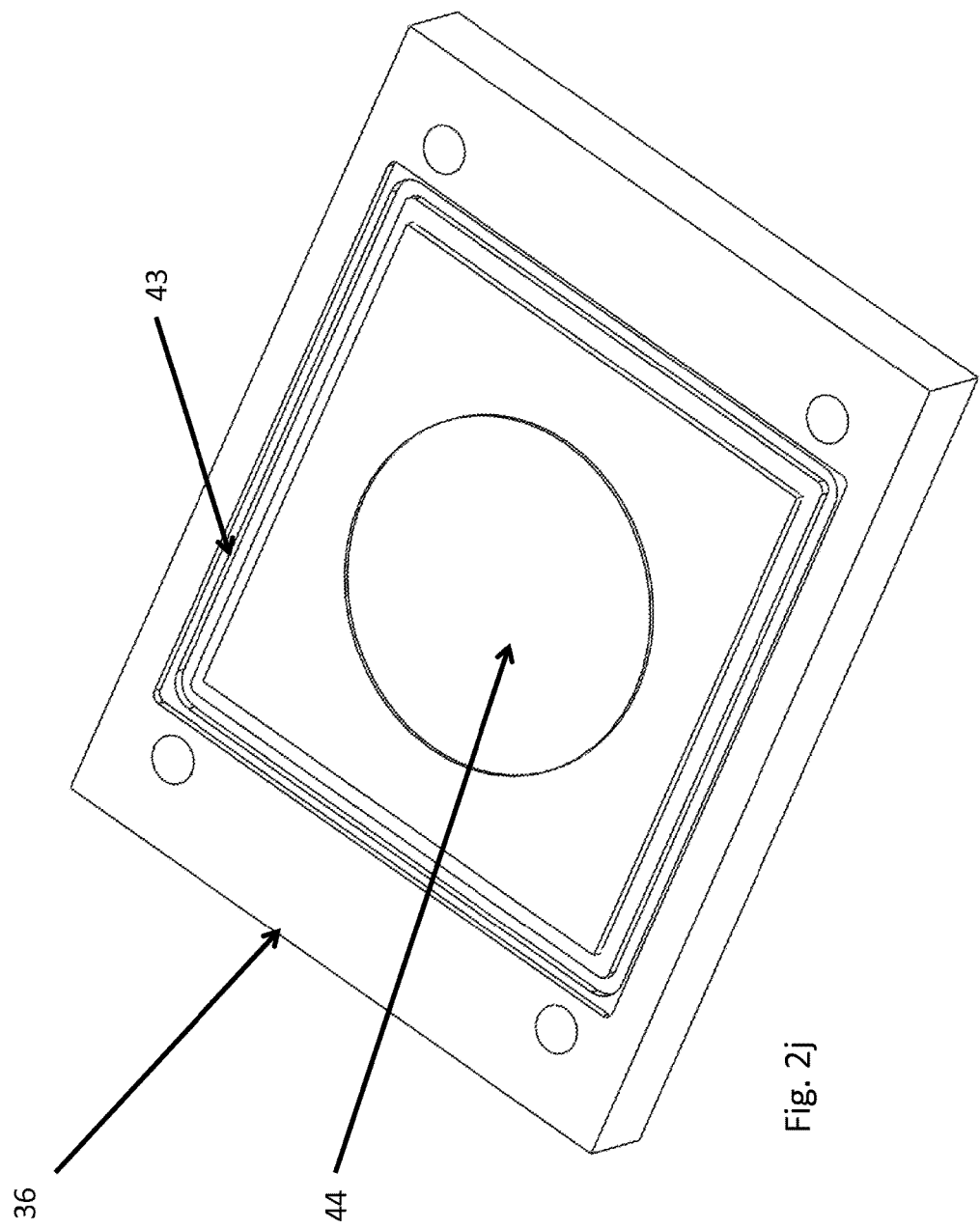

FIGS. 2a-2k illustrate multiple partial views of an exemplary embodiment of UNIT device 100. FIGS. 2a and 2b illustrate top and bottom perspective views, respectively, of reservoir tank 10. FIGS. 2c-2e illustrate perspective views of head tank 20 and soil cell 30. FIGS. 2f and 2g illustrate top and bottom perspective views, respectively, of head tank 20 and a top plate 34. FIGS. 2*h* and 2*i* illustrate top perspective and top views, respectively, of sample chamber 40. FIGS. 2*j* and 2*k* illustrate top perspective views of a bottom plate 36.

Fluid from various sources enters reservoir 10 through reservoir inlet 11 and exits through reservoir outlet 12 to head tank 20. Fluid from reservoir tank 10 enters head tank 20 through head inlet 21 and exits through head outlet 22 to soil cell 30. Soil cell 30 includes a base 31, a plurality of chamber and optional sensor posts 32*a* and 32*b*, a plurality of threaded nuts 33, at least one top plate 34, a cell inlet 35, at least one bottom plate 36, a cell outlet 37, an outlet valve 38, at least one vertical bender port 39 and sample chamber 40. The configuration of soil cell 30 prevents it from exerting pressure on the soil sample during testing, ensuring that testing occurs under conditions that more closely simulate in-situ environments.

Base 31 is a substantially planar section of material from which chamber and sensor posts 32*a* and 32*b* extend. The exemplary embodiment includes four chamber posts 32*a* interconnecting top plate 34 and bottom plate 36 to place sample chamber 40 between and in contact with top plate 34 and bottom plate 36. Other embodiments may increase or decrease the number of chamber posts 32*a*. Threading on an upper end of each chamber post 32*a* allows attachment of threaded nut 33 to prevent removal of top plate 34. In alternate embodiments, other types of contours may serve a similar securing function. The exemplary embodiment also includes two optional sensor posts 32*b* that support bender sensor pair 60. Other embodiments may increase or decrease the number of sensor posts 32*b*, or eliminate them altogether.

In the exemplary embodiment, top plate 34 and bottom plate 36 are substantially square polymeric or aluminum plates. In other embodiments, top plate 34 and bottom plate 36 may be alternate shapes to accommodate different cross-sections of sample chamber 40 or varying numbers of posts. Top plate 34 includes cell inlet 35, with bottom plate 36 including cell outlet 37. Fluid from head tank 20 enters sample chamber 40 through cell inlet 35 and exits through cell outlet 37 to reservoir tank 10. Outlet valve 38 controls fluid flow to reservoir tank 10. In the exemplary embodiment, outlet valve 38 is a ball valve that can be adjusted anywhere between completely closed and completely open. This simulates boundary conditions ranging from completely impermeable to free-draining. In certain embodiments, bottom plate 36 also includes drainage grooves etched into the surface, allowing more efficient drainage of fluid. In the exemplary embodiment, one or both of top plate 34 and bottom plate 36 include vertical bender port 39, which allow insertion of bender sensor pairs 60 into soil cell 30 to measure seismic wave propagation parallel to the direction of fluid flow. Top plate 34 also includes at least one pressure equalization port 48, which extends through top plate 34 to connect the interior of sample chamber 40 to the outside atmosphere. This keeps sample chamber 40 at atmospheric pressure during tests, ensuring that tests on soil samples occur under conditions that more closely simulate in-situ environments.

Sample chamber 40 is a modular unit made up of at least one chamber plate 41. In embodiments with more than one chamber plate 41, sealing gaskets 42 extend between chamber plates 41 to prevent fluid leakage. In the exemplary embodiment, chamber plates 41 are a substantially transparent material such as, by not limited to transparent acrylic while sealing gaskets 42 are a chemical-resistant, fluid-proof polymer. Sample chamber 40 may have a rectangular, square or circular cross-section. The ability to capture a source wavelength emitted by bender sensor pairs 60 dictates the shape of the cross-section, while the height of sample chamber 40 may be altered to allow for simulation of deeper soil levels. Sample chamber 40 is removable from between top plate 34 and bottom plate 36, allowing replacement. Certain embodiments of soil cell 30 include multiple interchangeable sample chambers 40 of varying heights, allowing for soil testing at different simulated depths.

O-rings 43 located between sample chamber 40 and top plate 34 and bottom plate 36 prevent fluid from leaking out of sample chamber 40. In the exemplary embodiment, O-rings 43 are located in grooves in top plate 34 and bottom plate 36 which receive upper and lower ends of sample chamber 40. Soil samples rest between a plurality of removable porous stone inserts 44 inset in top plate 34 and bottom plate 36 to ensure uniform distribution of flow and drainage.

In the exemplary embodiment, at least one horizontal bender port 45 in sample chamber 40 allows insertion of bender sensor pairs 60 into soil cell 30 to measure seismic wave propagation perpendicular to the direction of fluid flow. Each sample chamber 40 has a quasi-unique location of horizontal bender port or ports 45 to allow placement of bender sensor pairs 60 in any configuration possible. In one embodiment, a user may remove a complete sample chamber 40 from UNIT device 100 and replace it with another sample chamber 40 having a different location of horizontal bender port or ports 45. In another embodiment, a user need only replace one or more of chamber plates 41 to alter the location of horizontal bender port or ports 45.

A plurality of resistivity posts 46 radially project from one side of sample chamber 40. Resistivity sensor 70 connects to resistivity posts 46 to measure resistance as a proxy for fluid content of the soil sample. In the exemplary embodiment, resistivity posts 46 are steel posts. Two piezometer ports 47 are stacked vertically on the side of sample chamber 40 opposite resistivity posts 46. In the exemplary embodiment, piezometer ports 47 are vertically separated by approximately 50.8 mm. Piezometric sensor pairs 80 inserted into piezometer ports 47 measure the fluid pressure differential along the direction of fluid flow.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the terms "substantially" or "approximately" as used herein may be applied to modify any quantitative representation that could permissibly vary without resulting in a change in the basic function to which it is related.

What is claimed is:

1. A soil cell device, comprised of:
   a substantially planar base connected to a plurality of chamber posts;
   at least one top plate connected to said plurality of chamber posts, said at least one top plate having a cell inlet;
   at least one bottom plate connected to said plurality of chamber posts, said at least one bottom plate having a cell outlet;
   at least one sample chamber located between and in contact with said at least one top plate and said at least one bottom plate, said at least one sample chamber comprising at least one chamber plate;

at least one pressure equalization port extending through said at least one top plate;

a plurality of bender ports extending into said sample chamber; and a bender sensor pair extending into said sample chamber through said plurality of bender ports, wherein said at least one top plate and said at least one chamber plate are removable from said soil cell device.

2. The device of claim 1, wherein said plurality of chamber posts have a threaded upper end and receive a plurality of threaded nuts.

3. The device of claim 1, further comprising at least one sensor post connected to said base.

4. The device of claim 1, wherein said plurality of bender ports comprise at least one vertical bender port extending into said at least one top plate or said at least one top plate.

5. The device of claim 1, further comprising a plurality of O-rings located between an upper end of said at least one sample chamber and said top plate, and between a lower end of said at least one sample chamber and said bottom plate.

6. The device of claim 1, further comprising at least one groove located on said at least one top plate and at least one groove located on said at least one bottom plate, wherein said at least one groove located on said at least one top plate receives an upper end of said at least one sample chamber and wherein said at least one groove located on said at least one bottom plate receives a lower end of said at least one sample chamber.

7. The device of claim 1, wherein said cell outlet further comprises an outlet valve.

8. The device of claim 7, wherein said outlet valve comprises an adjustable ball valve.

9. The device of claim 1, wherein said at least one sample chamber has a cross section selected from the group consisting of circular and square.

10. The device of claim 1, wherein said at least one chamber plate comprises a plurality of chamber plates, wherein a plurality of sealing gaskets extend between said plurality of chamber plates.

11. The device of claim 1, wherein said plurality of bender ports comprise at least one horizontal bender port extending into said at least one sample chamber.

12. The device of claim 11, wherein said at least one sample chamber comprises a plurality of sample chambers, wherein each of said plurality of sample chambers comprises at least one horizontal bender port in a quasi-unique location.

13. The device of claim 11, wherein said at least one chamber plate comprises a plurality of chamber plates, wherein each of said plurality of chamber plates comprises at least one horizontal bender port in a quasi-unique location.

14. The device of claim 1, wherein said at least one sample chamber comprises a substantially transparent material.

15. The device of claim 1, wherein said at least one top plate and said at least one bottom plate further comprise a plurality of porous stone inserts.

16. The device of claim 1, wherein said at least one sample chamber further comprises a plurality of resistivity posts extending into said at least one sample chamber.

17. The device of claim 1, wherein said at least one sample chamber further comprises a plurality of piezometer ports extending into said at least one sample chamber.

18. An ultrasonic near-surface inundation testing (UNIT) device, comprised of:

a soil cell device, comprised of:

a substantially planar base connected to a plurality of chamber posts, at least one top plate connected to said plurality of chamber posts, said at least one top plate having a cell inlet, at least one bottom plate connected to said plurality of chamber posts, said at least one bottom plate having a cell outlet, at least one sample chamber located between and in contact with said at least one top plate and said at least one bottom plate, said at least one sample chamber comprising at least one chamber plate, at least one pressure equalization port extending through said at least one top plate, a plurality of bender ports extending into said sample chamber, and a bender sensor pair extending into said sample chamber through said plurality of bender ports, wherein said at least one top plate and said at least one chamber plate are removable from said soil cell device;

at least one head tank comprising a head inlet, a head outlet and an overflow outlet, wherein said overflow outlet is located at a first height above a bottom of said head tank; and at least one reservoir tank comprising a reservoir inlet and a reservoir outlet, wherein said at least one reservoir tank has a greater fluid capacity than said head tank, at least one recirculating pump, wherein said reservoir outlet is connected to said head inlet, wherein said overflow outlet is connected to said reservoir inlet, wherein said head outlet is connected to said cell inlet, wherein said cell outlet is connected to said recirculating pump, and wherein said recirculating pump is connected to said reservoir inlet.

19. The device of claim 18, further comprising at least one resistivity sensor or piezometric sensor pair.

20. The device of claim 18, wherein said at least one head tank comprises a plurality of head tanks, wherein each of said plurality of head tanks has an overflow outlet located at a quasi-unique height.

* * * * *